(12) United States Patent
Campbell et al.

(10) Patent No.: US 10,486,156 B2
(45) Date of Patent: Nov. 26, 2019

(54) FLUID TRANSFER FROM DIGITAL MICROFLUIDIC DEVICE

(71) Applicant: DH Technologies Development PTE Ltd., Singapore (SG)

(72) Inventors: John Lawrence Campbell, Milton (CA); Kihwan Choi, Daeijeon (KR); Yves LeBlanc, Newmarket (CA); Chang Liu, Richmond Hill (CA); Aaron Wheeler, Toronto (CA)

(73) Assignees: DH Technologies Development Pte. Ltd. (SG); University of Toronto (CA)

( * ) Notice: Subject to any disclaimer, the term of this patent is extended or adjusted under 35 U.S.C. 154(b) by 177 days.

(21) Appl. No.: 15/309,275

(22) PCT Filed: May 6, 2015

(86) PCT No.: PCT/IB2015/053313
§ 371 (c)(1),
(2) Date: Nov. 7, 2016

(87) PCT Pub. No.: WO2015/170268
PCT Pub. Date: Nov. 12, 2015

(65) Prior Publication Data
US 2017/0072397 A1     Mar. 16, 2017

Related U.S. Application Data

(60) Provisional application No. 61/991,062, filed on May 9, 2014.

(51) Int. Cl.
*B01L 3/00*      (2006.01)
*B01F 13/00*   (2006.01)
(Continued)

(52) U.S. Cl.
CPC .... *B01L 3/502792* (2013.01); *B01F 13/0071* (2013.01); *B01F 13/0076* (2013.01);
(Continued)

(58) Field of Classification Search
None
See application file for complete search history.

(56) References Cited

U.S. PATENT DOCUMENTS 8,389,297 B2 *  3/2013  Pamula ................ C12Q 1/6869
                                                            435/283.1
2006/0039823 A1   2/2006  Yamakawa et al.
(Continued)

FOREIGN PATENT DOCUMENTS

WO       2014062551       4/2014

OTHER PUBLICATIONS

Samiei et al. (Lab. Chip, 16, 2376) (Year: 2016).*
(Continued)

*Primary Examiner* — Gurpreet Kaur
*Assistant Examiner* — Steven E Rosenwald (57) ABSTRACT

Methods and systems for processing fluids utilizing a digital microfluidic device and transferring droplets from the digital microfluidic device to a downstream analyzer are described herein. Methods and systems in accordance with the present teachings can allow for the withdrawal of fluid from a digital microfluidic device, and can in some aspects enable the integration of a digital microfluidic device as a direct, in-line sample processing platform from which a droplet can be transferred to a downstream analyzer.

11 Claims, 6 Drawing Sheets

(51) Int. Cl.
  *G01N 27/447* (2006.01)
  *G01N 30/16* (2006.01)
  *G01N 35/00* (2006.01)

(52) U.S. Cl.
  CPC ....... *G01N 27/44791* (2013.01); *G01N 30/16* (2013.01); *G01N 35/00871* (2013.01); *B01L 2300/0645* (2013.01); *B01L 2300/0887* (2013.01); *B01L 2400/0415* (2013.01); *B01L 2400/0427* (2013.01); *G01N 2030/162* (2013.01)

(56) References Cited

U.S. PATENT DOCUMENTS

| | | | |
|---|---|---|---|
| 2006/0166373 A1 | 7/2006 | Enoki et al. | |
| 2008/0185339 A1* | 8/2008 | Delapierre | B01D 11/04 210/634 |
| 2009/0321262 A1 | 12/2009 | Adachi et al. | |
| 2010/0307917 A1* | 12/2010 | Srinivasan | B01L 3/0268 204/450 |
| 2011/0053798 A1* | 3/2011 | Hindson | C12Q 1/6844 506/12 |
| 2011/0091989 A1 | 4/2011 | Sista et al. | |
| 2011/0107822 A1* | 5/2011 | Bunner | B01L 3/502792 73/61.52 |
| 2011/0303542 A1* | 12/2011 | Srinivasan | B01L 3/502792 204/548 |
| 2012/0083046 A1 | 4/2012 | Watson et al. | |
| 2012/0085645 A1 | 4/2012 | Mousa et al. | |
| 2012/0283140 A1* | 11/2012 | Chu | B01J 19/0046 506/16 |
| 2013/0068622 A1* | 3/2013 | Schertzer | G01N 27/04 204/600 |
| 2013/0134040 A1* | 5/2013 | Lee | G01N 27/44791 204/451 |
| 2013/0164856 A1 | 6/2013 | Jebrail et al. | |
| 2014/0001202 A1 | 1/2014 | Vann et al. | |
| 2015/0212043 A1* | 7/2015 | Pollack | G01N 27/44791 204/451 |

OTHER PUBLICATIONS

Jebrail et al. (Lab Chip, 11, 3218) and supplemental materials (Year: 2011).*
International Search Report and Written Opinion for PCT/IB2015/053313 dated Jul. 28, 2015.

* cited by examiner

FLUID TRANSFER FROM DIGITAL MICROFLUIDIC DEVICE

RELATED APPLICATION

This application claims priority to U.S. provisional application No. 61/991,062, filed on May 9, 2014, which is incorporated herein by reference in its entirety.

FIELD

The present teachings generally relate to processing fluids and, more particularly, to methods and apparatus for transferring fluids from a digital microfluidic device.

INTRODUCTION

The use of fluids on a micro- and macro-scale has facilitated advancements in many technological fields, including ink jet printing, medical implants, sample preparation for mass spectrometers and gas chromatographs, industrial process control equipment, and lab-on-a-chip applications, in which biological assays and chemical analysis are performed on a microchip-sized wafer of glass, plastic, or silicon. In general, macro-scale fluid processing involves working with volumes in the milliliter range, while micro-scale fluid processing involves working with volumes of less than 1 millimeter, such as volumes in the microliter, nanoliter, and/or picoliter range.

The field of microfluidics has grown and developed to precisely and efficiently transport, mix, and analyze fluids on a micro-scale. Common fluids used in microfluidic devices include whole blood samples, bacterial cell suspensions, protein or antibody solutions, analyte solutions, and buffers. Microfluidic devices can be used alone or in combination with analytical equipment to obtain a variety of measurements concerning the microfluids or combinations thereof, including molecular diffusion coefficients, fluid viscosity, pH, chemical binding coefficients, and enzyme reaction kinetics. Other applications for microfluidic devices include capillary electrophoresis, isoelectric focusing, immunoassays, flow cytometry, sample injection of proteins for analysis via mass spectrometry, PCR amplification, DNA analysis, cell manipulation, cell separation, cell patterning, and chemical gradient formation.

Conventional or "channel-based" microfluidic systems include fluid reservoirs and networks of micron-dimensional channels. In these systems, methods to reliably merge, mix, split, and dispense the fluids are important for performance of the analysis. Typical methods and devices to aliquot a sample from a fluid reservoir through one or more channels include capillary action, valves, micro-pumps (e.g., syringe pumps, electro-osmotic pumps), and micro-pipettes.

Unlike conventional microfluidics that typically utilize channels containing a continuous flow therethrough, digital microfluidics (DMF) enables the processing of single isolated droplets through the electric manipulation of fluid droplets on electrode arrays (e.g., via electrowhetting or dielectrophoresis). When appropriate potentials are applied to the electrodes, the droplets may be driven to mix, merge, split, and/or be dispensed from fluid reservoirs. Sample and reagent droplets with volumes of less than one microliter can thus be moved in multiple and reconfigurable paths defined by the actuation sequence of the electrode array. Indeed, each droplet can be controlled individually without the need for networks of channels, pumps, valves, or mechanical mixers. Moreover, various processes can be performed simultaneously with a simple and compact design.

Like conventional microfluidic devices, DMF can provide low reagent consumption and fast heat transfer, and has been demonstrated for diverse applications including cell based assays, enzyme assays, protein profiling, and polymerase chain reaction. However, in applications in which the DMF is utilized as a front-end fluid processing system for further downstream analysis (e.g., via LC, MS, or LC-MS), the DMF system and downstream analyzer can be difficult to integrate into an automated system. That is, manual, off-line steps are generally used to transfer the individual droplets sandwiched between the plates of a DMF system into a downstream analyzer. Such manual transfer steps can lead to adsorption, contamination, and sample loss.

Accordingly, there remains a need for methods and systems that can efficiently transfer and/or sample droplets following processing by a DMF system.

SUMMARY

Apparatus, systems, and methods in accordance with the applicant's present teachings allow for the withdrawal of fluid from a digital microfluidic device, and can in some aspects enable the integration of a digital microfluidic device as a direct, in-line sample processing platform from which a droplet can be transferred to a downstream analyzer (e.g., LC or MS). Although various aspects of the invention are discussed herein with reference to transferring a fluid sample from a digital microfluidic device to a downstream analysis device, the invention can have broader applicability, e.g., for withdrawing a fluid volume sandwiched between two plates to another device or to an open surface.

In accordance with various aspects of the applicant's teachings, a method of processing a sample is provided that includes disposing a sample droplet between top and bottom plates of a digital microfluidic device, forming an extraction droplet in a sampling hole extending through one of the top and bottom plates, and contacting the sample droplet and the extraction droplet with one another so as to form a merged droplet that is at least partially disposed in the sampling hole. By way of example, cohesive forces between molecules in the sample droplet and the extraction droplet are effective to merge the sample droplet and extraction droplet upon contact. At least a portion of the merged droplet can then be removed from the digital microfluidic device via the sampling hole (e.g., for transfer to another analysis device such as a mass spectrometer, LC column, capillary electrophoresis device, or flow cytometer).

In some aspects, at least one of the top and bottom plates can include an electrode array configured to manipulate movement of the sample droplet. By way of example, in some aspects, the method can include moving the sample droplet toward the sampling hole by actuating one or more actuation electrodes associated with the bottom plate. For example, the sample droplet can be manipulated to be disposed adjacent the sampling hole. In related aspects, a plurality of actuation electrodes can be disposed within the bottom plate such that the voltages applied thereto can be controlled so as to move the sample droplet. Accordingly, in accordance with various aspects, the sample droplet can be contacted with the extraction droplet by moving the sample droplet toward said sample droplet formed in said sampling hole. Alternatively or additionally, contacting the sample droplet with the extraction droplet can comprise moving the sample droplet to a position adjacent the sampling hole and forming the extraction droplet in the sampling hole with a sufficient volume such that the extraction droplet contacts said sample droplet. By way of example, the method can include increasing a volume of an extraction droplet until the extraction droplet contacts the sample droplet disposed adjacent the sampling hole. For example, the volume of the extraction droplet can be greater than the sampling hole such that at least a portion of the sample droplet extends between the top and bottom plates.

In accordance with various aspects, removing the merged droplet from the digital microfluidic device can comprise aspirating the merged droplet via the sampling hole. By way of non-limiting example, a sampling needle can be extended into the merged droplet. In some aspects, an autosampler can be utilized to aspirate the merged droplet. In related aspects, the autosampler can also be utilized to form the extraction droplet in the sampling hole.

In some aspects, each of the top and bottom plates comprises a planar surface in contact with the sample droplet, and the sampling hole extends along an axis substantially perpendicular to the planar surfaces. The sampling hole can extend through the top plate, for example.

In some aspects, the sample droplet and the extraction droplet can have substantially equivalent volumes. In various aspects, the merged droplet can have a large enough volume that it can extend through the sampling hole, for example.

In accordance with various aspects of the applicant's teachings, a system for processing a sample is provided that includes a digital microfluidic device, comprising opposed top and bottom plates defining a space therebetween for containing a sample droplet, at least one of said top and bottom plates having a sampling hole extending therethrough in fluid communication with the space and configured to receive an extraction droplet. The digital microfluidic device can also include a plurality of actuation electrodes associated with at least one of the top and bottom plates, wherein the plurality of actuation electrodes are configured to manipulate the sample droplet such that the sample and extraction droplets can contact one another so as to form a merged droplet at least partially disposed in the sampling hole. The system can also include a fluid handling system configured to extract the merged droplet from the digital microfluidic device via the sampling hole. In some aspects, an analysis device (e.g., a mass spectrometer or LC column) can be configured to receive the extracted merged droplet from the fluid handling system. In various aspects, the present teachings can thus enable in-line (e.g., automated) transfer of a sample from the digital microfluidic device to a downstream analysis device for further processing. For example, the fluid handling system can be an autosampler. In some aspects, the fluid handling system can also be configured to form the extraction droplet within the sampling hole.

In accordance with various aspects, the plurality of actuation electrodes can be configured to move the sample droplet into contact with an extraction droplet at least partially disposed in the sampling hole.

In some aspects, the fluid handling system can also be configured to form the extraction droplet within the sampling hole. In related aspects, for example, the plurality of actuation electrodes can be configured to move the sample droplet adjacent to the sampling hole and the fluid handling system can be configured to form the extraction droplet in the sampling hole with a sufficient volume such that the extraction droplet contacts said sample droplet. By way of example, the fluid handling system can be configured to increase a volume of the extraction droplet until the extraction droplet contacts the sample droplet.

In some aspects, the system can additionally include a controller configured to control the actuation electrodes and/or the fluid handling system. By way of example, the controller can be coupled to the plurality of actuation electrodes and be configured to apply one or more electrical signals to the actuation electrodes so as to manipulate the sample droplet within the digital microfluidic device. Additionally, in some aspects, the system can also include at least one memory operatively coupled to the controller, the at least one memory configured to store at least one sample processing protocol for execution by the controller.

In accordance with various aspects of the applicant's teachings, a method of processing a fluid is provided that includes disposing a first droplet between a top plate and a bottom plate, forming a second droplet in a sampling hole extending through one of the top and bottom plates, contacting the first and second droplets with one another so as to form a merged droplet at least partially disposed in said sampling hole, and removing at least a portion of the merged droplet from the sampling hole. In some aspects, the bottom and top plates can be configured to have an electric field generated in the space therebetween.

In accordance with various aspects of the applicant's teachings, a method of processing a sample is provided that includes disposing a sample droplet between a top plate and a bottom plate, extending a sampling needle into a sampling hole extending through one of the top and bottom plate in a position opposed to an electrode associated to the other of the top and bottom plate, applying an electric potential to at least one of the sampling needle and the electrode so as to generate an electric field in the space between the top and bottom plates in the position, and removing at least a portion of the merged droplet from the sampling hole. In some aspects, the method can also include aspirating the sample droplet while applying the electric potential. Alternatively or additionally, the sampling needle can be biased relative to the electrode so as to attract the sample droplet.

In accordance with various aspects of the applicant's teachings, a method of processing a sample is provided comprising disposing a sample droplet between a top plate and a bottom plate of a digital microfluidic device, and removing at least a portion of the droplet from the digital microfluidic device via a sampling hole extending through the plate.

In accordance with various aspects, the method further can comprise pre-filling the sampling hole with an aqueous solution to form an extraction droplet in the sampling hole, contacting the sample droplet and the extraction droplet with one another so as to form a merged droplet at least partially disposed in the sampling hole, wherein at least a portion of the merged droplet is removed from the digital microfluidic device via the sampling hole. In accordance with various aspects, the aqueous solution does not need to be limited to a pure aqueous solution, but can also be a mixture that is predominantly water but can also contain a small amount of organic solvent or any suitable mixture can be used.

In accordance with various aspects, the method further can comprise transferring the merged droplet to an analysis device.

In some aspects, the method further can comprise moving the sample droplet toward the sampling hole by actuating one or more actuation electrodes associated with the bottom plate. In some aspects, moving the sample droplet toward the sampling hole can comprise manipulating the sample droplet to be disposed adjacent the sampling hole.

In some aspects, a plurality of actuation electrodes can be disposed within the bottom plate, and actuating the plurality of actuation electrodes can comprise controlling the voltages applied to the different actuation electrodes so as to move the sample droplet. In some aspects, at least one of the top and bottom plates can comprise an electrode array configured to manipulate movement of the sample droplet.

In various aspects, the method further can comprise increasing a volume of the extraction droplet until the extraction droplet contacts the sample droplet.

In some aspects, removing the merged droplet from the digital microfluidic device can comprise aspirating the merged droplet via the sampling hole by extending a sampling needle into the merged droplet through the sampling hole.

In some aspects, an autosampler can be utilized to form the extraction droplet in the sampling hole.

In some aspects, the sample droplet can comprise a mixture of water and an organic solvent. In some aspects, the sample droplet can comprise a mixture of about 70% water and about 30% methanol. In some aspects, the sample droplet can comprise a surfactant.

In accordance with various aspects, a system for processing a sample is provided that includes a digital microfluidic device, comprising opposed top and bottom plates defining a space therebetween for containing a sample droplet, the plate having a sampling hole, and a fluid handling system can be configured to extract at least a portion of the droplet from the digital microfluidic device via the sampling hole.

In accordance with various aspects, the system further can comprise the sampling hole extending therethrough in fluid communication with the space, the sampling hole can be configured to receive an extraction droplet comprising an aqueous solution, a plurality of actuation electrodes can be associated with at least one of the top and bottom plates, wherein the plurality of actuation electrodes can be configured to manipulate the sample droplet such that the sample droplet and the extraction droplet contact one another so as to form a merged droplet at least partially disposed in the sampling hole, wherein at least a portion of the merged droplet can be extracted from the digital microfluidic device via the sampling hole. In accordance with various aspects, the aqueous solution does not need to be limited to a pure aqueous solution, but can also be a mixture that is predominantly water but can also contain a small amount of organic solvent or any suitable mixture can be used.

In accordance with various aspects, the system further can comprise an analysis device configured to receive the extracted merged droplet from the fluid handling system. In various aspects, the fluid handling system can comprise an autosampler. In various aspects, the fluid handling system further can be configured to form the extraction droplet within the sampling hole, the plurality of actuation electrodes can be configured to move the sample droplet adjacent to the sampling hole, and the fluid handling system can be configured to form the extraction droplet in said sampling hole with a sufficient volume such that said extraction droplet contacts said sample droplet, and the fluid handling system can be configured to increase a volume of the extraction droplet until the extraction droplet contacts the sample droplet.

In accordance with various aspects, the system further can comprise at least one memory operatively coupled to the controller, the at least one memory can be configured to store at least one sample processing protocol for execution by the controller.

In accordance with various aspects, a method of processing a fluid can be provided comprising disposing a sample droplet between a top plate and a bottom plate, extending a sampling needle into a sampling hole extending through one of the top and bottom plate in a position opposed to an electrode associated to the other of the top and bottom plate, applying an electric potential to at least one of the sampling needle and the electrode so as to generate an electric field in the space between the top and bottom plates in the position, removing at least a portion of the merged droplet from the sampling hole, aspirating the sample droplet while applying the electric potential, and biasing the sampling needle relative to the electrode so as to attract the sample droplet.

These and other features of the applicants' teachings are set forth herein.

BRIEF DESCRIPTION OF THE DRAWINGS

The skilled person in the art will understand that the drawings, described below, are for illustration purposes only. The drawings are not intended to limit the scope of the applicants' teachings in any way. For convenience, reference numerals may also be repeated (with or without an offset) throughout the figures to indicate analogous components or features.

DETAILED DESCRIPTION

It will be appreciated that for clarity, the following discussion will explicate various aspects of embodiments of the applicants' teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicants' teachings may not require certain of the specifically described details in every implementation, which are set forth herein only to provide a thorough understanding of the embodiments. Similarly it will be apparent that the described embodiments may be susceptible to alteration or variation according to common general knowledge without departing from the scope of the disclosure. The following detailed description of embodiments is not to be regarded as limiting the scope of the applicants' teachings in any manner.

Various terms are used herein consistent with their customary meanings in the art. Typically, the term "about" as used herein means greater or lesser than the value or range of values stated by 1/10 of the stated values, e.g., ±10%. For instance, a concentration value of about 30% can mean a concentration between 27% and 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

The present teachings generally relate to the transfer of fluids from a fluid processing system configured to mix, separate, suspend, filter, or otherwise process micro-volumes of fluids and/or prepare the fluid for further downstream analysis (e.g., via liquid chromatography and/or mass spectrometry). In some aspects, systems and methods in accordance with the applicant's present teachings allow for the withdrawal of fluid from a digital microfluidic device, and can enable the integration of a digital microfluidic device as a direct, in-line sample processing platform from which a droplet can be transferred to a downstream analyzer. Though devices described herein generally process fluid volumes below the milliliter range (e.g., microliters, picoliters, or nanoliters), it will be appreciated in light of the present teachings that the fluid processing systems may process any fluid volume suitable for use in embodiments described herein.

Figure 1:
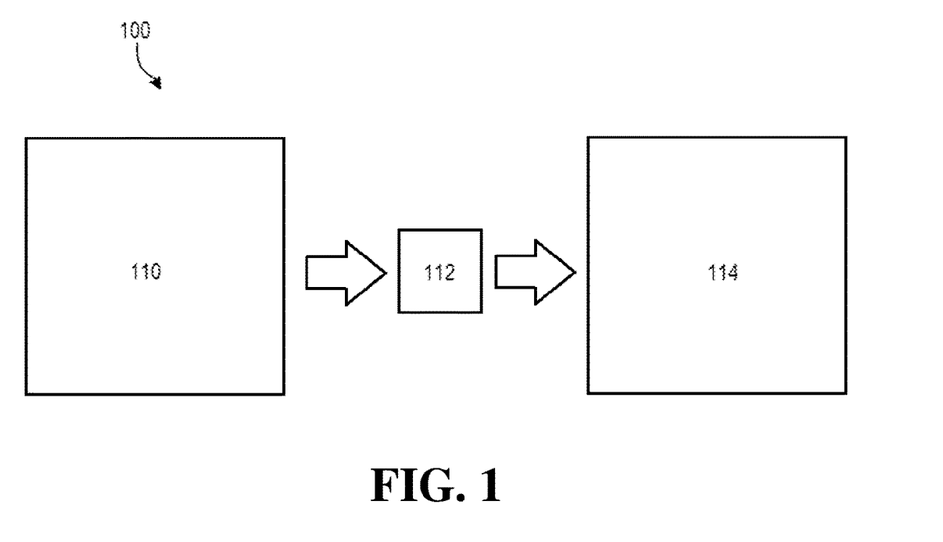
FIG. 1, in schematic diagram, depicts an exemplary system in accordance with various aspects of the applicants' teachings.

With reference first to FIG. 1, an exemplary system in accordance with various aspects of the present teachings is illustrated schematically. As shown in FIG. 1, the system 100 generally comprises a first fluid processing system 110 configured to provide a liquid sample (e.g., a fluid droplet containing one or more analytes of interest), a second fluid processing system 112 (e.g., an analyzer) configured to further process and/or analyze the liquid sample generated by the first fluid processing system, and a fluid handling system 112 for fluidly coupling and/or transferring the liquid sample from the first fluid processing system 110 to the second fluid processing system 114.

It will be appreciated in light of the present teachings that the fluid handling system can have a variety of configurations, but generally is configured to withdraw a sample (e.g., a sample droplet) from the first fluid processing system 110 and/or transfer the sample from the first fluid processing system 110 to the second fluid processing system 114. The fluid handling system 112 can include, for example, one or more fluidic coupling elements such that the first and second fluid processing systems 110, 114 are coupled via one or more fluidic pathways. By way of example, the fluid handling system 112 can comprise any number of channels, conduits, valves, and/or pumps (e.g., micro-pumps such as syringe pumps, electro-osmotic pumps) for delivering the sample to the downstream fluid processing system 114. It will also be appreciated that though the present teachings also enable a user to manually withdraw the sample from the first fluid processing system 110 via aspiration with a pipette, for example, systems in accordance with the present teachings can utilize fluid handling robots to withdraw and/or transfer fluids. By way of non-limiting example, a liquid handling robot under the control of a controller and equipped with a pipette tip (e.g., a micropipette) or syringe could be utilized to provide for the automated transfer of the sample between the first and second fluid processing systems 110, 114. For example, any commercially-available auto-sampler suitable for intaking samples such as the Eksigent NanoLC-AS1 Autosampler, and Eksigent NanoLC-AS2 Autosampler, and modified in accordance with the present teachings could be used to withdraw and/or transfer the sample. Moreover, as will be discussed in detail below, in some aspects the fluid handling system 112 can additionally be configured to dispense a fluid (e.g., form an extraction droplet) in the first fluid processing system 110.

The second fluid processing system 114 can also have a variety of configurations, but is generally configured to receive the processed sample output by the first fluid processing system 110, for example, via the fluid handling system 112 and/or analyze the sample. While the systems, devices, and methods described herein can be used in conjunction with any fluid analyzer known in the art and modified in accordance with the present teachings, in some exemplary aspects, the second fluid processing system 112 can be a liquid chromatography (LC) column, mass spectrometer (MS), or combinations thereof (e.g., LC-MS/MS), all by way of non-limiting example. Other exemplary downstream fluid processing systems for use in the present teaching include capillary electrophoresis (CE), gas chromatography (GC), flow cytometry devices, etc., or combinations thereof. In some aspects, the fluid handling system 112 can transfer the sample from the first fluid processing system 110 to a second fluid processing system 114 such as a microarray plate, or another microfluidic device for further sample handling and/or analysis.

Figure 2A:
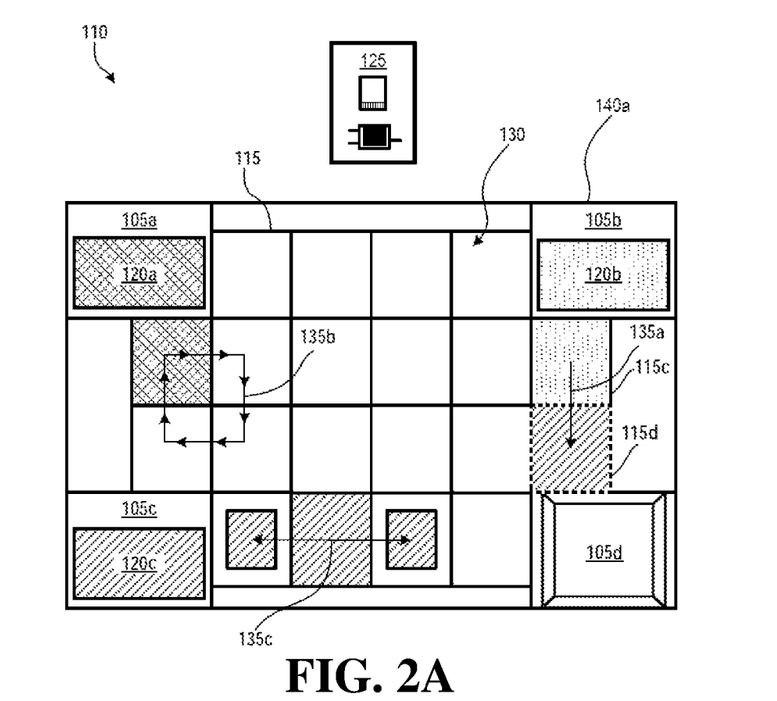
FIG. 2A, in schematic diagram, depicts an exemplary bottom plate of a digital microfluidic device for use in the system of FIG. 1 in accordance with various aspects of the applicants' teachings.
Figure 2B:
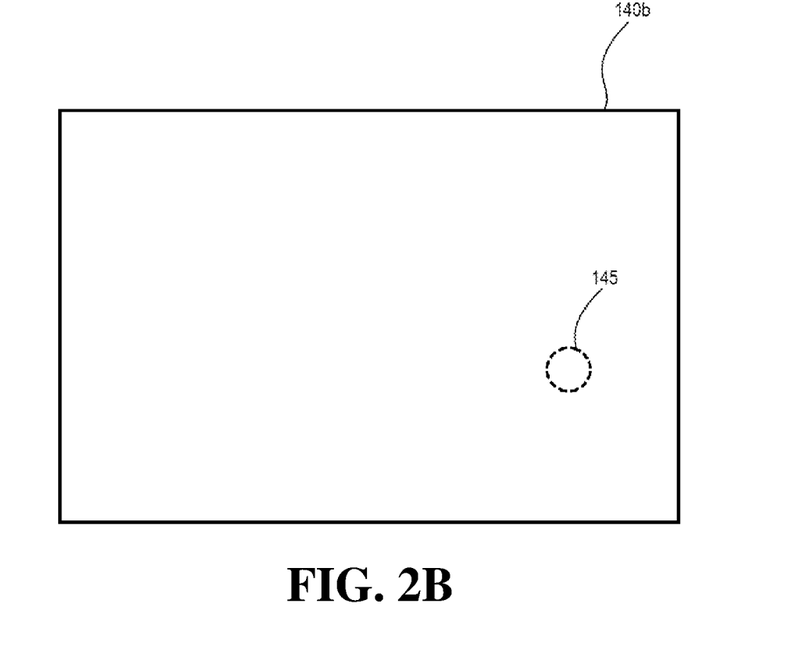
FIG. 2B, in schematic diagram, depicts an exemplary top plate of a digital microfluidic device for use in the system of FIG. 1 in accordance with various aspects of the applicants' teachings.
Figure 3:
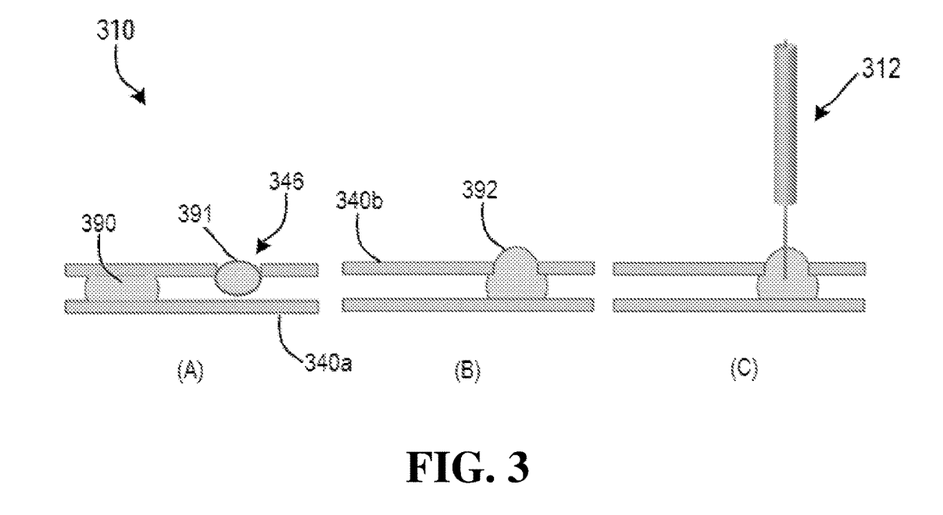
FIG. 3, in schematic diagram, depicts an exemplary method for transferring droplets from a digital microfluidic device in accordance with various aspects of the applicants' teachings.

With reference now to FIGS. 2A-2B and 3, a first fluid processing system 110 in the form of an exemplary digital microfluidic device in accordance with various aspects of the present teachings is illustrated schematically. It should be understood that the exemplary digital microfluidic device 110 represents only one possible fluid processing system for use in accordance with embodiments of the systems, devices, and methods described herein, and fluid processing systems having other configurations and operational characteristics modified in accordance with the present teachings can alternatively be used with the systems, devices and methods described herein. Additional details of one exemplary digital microfluidic device for use in accordance with the present teachings are provided in U.S. Patent Pub. No. 20130143312 of Wheeler et al., the teachings of which are incorporated by reference in its entirety.

With specific reference now to FIGS. 2A and 2B, a microfluidic device 110 which may be used, for example, for sample preparation and/or droplet-based assays, such as cell culture and cell assays, using digital microfluidics is depicted. The digital microfluidic device 110 generally comprises a bottom plate 140a and a top plate 140b that are spaced apart from one another so as to define a volume within which one or more fluid droplets can be manipulated as discussed in detail below.

With reference first to the bottom plate 140a depicted in FIG. 2A, the bottom plate 140a of the digital microfluidic device 110 can include reservoir electrodes 105a-d configured to contain various fluids 120a-c, including, without limitation, reagents, buffers, solvents, magnetic beads, biological samples (e.g., cells), chemical samples, dyes, wash solutions, and any other fluid capable of operating according to the present teachings described herein. Reservoir electrode 105d, for example, can be utilized to contain waste fluids generated by the microfluidic device 110. It will also be appreciated that the fluids to be used in the digital microfluidic device 110 can be contained by a fluid source (not shown) external to device 110 and can be delivered thereto via pipettes, robotic dispensers, microprinters and microstamps, by way of non-limiting examples. By way of example, the reservoirs 105a-c could be part of a cartridge (not shown) that can couple to the digital microfluidic device 110 and that is in flow communication with the hydrophobic/dielectric surface above the array of actuating electrodes, as discussed in detail below.

As will be appreciated by a person skilled in the art, the fluids 120a-c can be dispensed onto a fluid surface 130 of actuating electrodes 115 adjacent to the reservoir electrodes 105a-c by applying voltages to the electrodes 115 and/or to the reservoir electrodes 105a-c. In some aspects, for example, a single droplet of a fluid 120a-c can be dispensed onto the fluid surface 130. In some embodiments, a single droplet of a fluid 120a-c may have a volume in the picoliter to microliter range, e.g., about 150 nanoliters (nL) of fluid.

As indicated above, the fluid surface 130 can include a plurality of actuating electrodes 115 (e.g., an array of actuating electrodes). Although FIG. 2A depicts multiple actuating electrodes 115, only one is labeled in FIG. 2A for simplification. Voltages may thus be applied to the actuating electrodes 115 to manipulate the fluids 120a-c within the microfluidic device 110 (e.g., to move the fluids 120a-c around the fluid surface 130). For instance, the fluids 120a-c can be moved from one electrode 115c to another electrode 115d by applying a voltage to one or more electrodes 115 of the electrode array, as indicated schematically by the arrow 135a. Also as schematically depicted in FIG. 2A, the microfluidic device 110 can be effective to mix fluids 135b and/or split/combine fluids 135c through actuation of various electrodes 115 and sequences and/or combinations thereof.

Generally, the fluid surface 130 can include the electrode array 105a-c, 115 which is coated with a layer of a hydrophobic insulator, such as Teflon® AF or Cytop®. The reservoir electrodes 105a-c may be configured to hold multiple units (e.g., multiple droplets) of fluid 120a-c, while each of the actuating electrodes 115 can be configured to hold less units of fluid 120a-c, such as one to three droplets. In some embodiments, electrical contact pads (not shown) can be connected to the electrodes 105a-c, 115 to enable the electrodes 105a-c, 115 to be individually addressed or actuated. The electrodes 105a-c, 115 can be formed from various materials, including copper, gold, platinum, chromium, and combinations thereof.

As shown in FIG. 2A, in some aspects, the microfluidic device 110 can additionally include a controller 125 in electrical communication with the reservoir electrodes 105a-c, actuating electrodes 115, and/or other components of the microfluidic device 110, such as one or more power supplies (not shown) for applying apply voltages to the electrodes. In some embodiments, for example, the controller 125 can provide control signals to the power supplies to coordinate the motion of fluids 120a-c on the fluid surface 130. It will be appreciated by those skilled in the art that the controller 125 can be implemented using known electrical components, such as suitable integrated circuits, and known engineering methods, modified in accordance with the present teachings. For example, the controller 125 can include one or more processors, memory modules, communication modules for communicating with the components of the microfluidic device 110 as well as software instructions for implementing the present teachings.

Figure 2C:
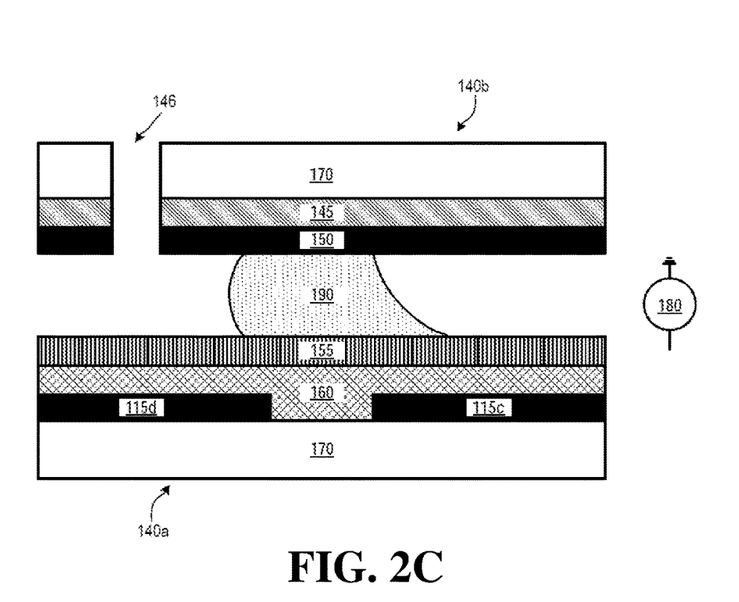
FIG. 2C, in schematic diagram, depicts a side view of the exemplary digital microfluidic device of FIGS. 2A and 2B.

With reference now to FIGS. 2B and 2C, the exemplary electrodes 115c,d of the lower plate 140a can be arranged on a substrate layer 170 and can be separated from each other by a dielectric material 160 (e.g., parylene-C) such that individual signals can be applied to the electrodes 115c,d. In some embodiments, the microfluidic device 100 can have more than one dielectric layer 160. As indicated above, a hydrophobic layer 155 (e.g., Teflon®, Cytop®, or the like) can be formed on top of dielectric material 160.

The top plate 140b can have a variety of configurations but is generally disposed above the bottom plate 140a and comprises a lower surface 150 that is configured to contact a fluid droplet 190 disposed between the bottom and top plates 140a,b. As best shown in the cross sectional view of microfluidic device 110 of FIG. 2C, the exemplary top plate 140b can be disposed in a facing relationship with the bottom plate 140b and includes a lower surface 150 that is spaced apart from the hydrophobic layer 155 of the bottom plate 140b. It will appreciated that the lower surface 150 and the upper surface 155 can be substantially planar and can be separated by a variety of distances (e.g., about 140 μm, about 280 μm).

As shown in FIG. 2C, the top plate 140b can include a substrate 170 and a plurality of reference electrodes (or a continuous reference electrode 145) associated therewith that can be biased to a potential (e.g., ground) different from the actuating potential applied to the electrodes 115 of the bottom plate 140a. In some aspects, the lowermost layer 150 of the top plate 140b can comprise a hydrophobic material 150, for example, that can be coated on reference electrode 145. Liquid droplets 190 can thus be arranged (e.g., sandwiched) between hydrophobic layers 150 and 155. Electrodes 115, voltage source 180, and the continuous reference electrode 145 can together form an electric field, which can be digitally manipulated by the controller 125, for example, to control the manipulation of the droplet 190.

As shown in FIGS. 2B and 2C, the top plate 140b can additionally include a through-hole 146, for example, that extends through the substrate 170, reference electrode 145, and hydrophobic layer 150 of the top plate 140b so as to provide access to the space defined by the opposed bottom and top plates 140a,b. It will be appreciated that though the through hole 146 is depicted as being disposed centered over electrode 115d, the through hole can extend through the top plate 140b at a variety of positions relative to the electrodes 115. By way of example, the through hole 146 can extend through the top plate 140b at a position substantially above and between the electrodes 115c,d. Moreover, though the through hole 146 is depicted as extending along an axis that is perpendicular to the planar inner surfaces of the bottom and top plates 140a,b, it will also be appreciated that the through hole 146 can extend through the top plate 140b at any angle that provides access to the space between the bottom and top plates 140a,b in accordance with the present teachings. It will further be appreciated that the through hole 146 can be formed using a variety of methods (e.g., drilled through top plate 140b) and can have a variety of shapes such as circles, ovals, squares, etc. that can be formed in the top plate 140b. Additionally, in some aspects, the interior of the through hole 146 can be coated, for example, with a hydrophilic material to promote the movement of the fluid droplet 190 therein, as discussed in detail below.

As a result of the through hole 146 in the reference electrode 145 of the top plate 140b (e.g., via distortions of the electric field), however, it can be difficult to position the fluid droplet 190 fully on electrode 115d, for example. As such, it can be difficult to transfer the droplet 190 from the microfluidic device 110 via a sampling needle or pipette that can be manipulated through the through hole 146, depending, for example, on the characteristics of the microfluidic device 110 (e.g., inter-plate spacing, strength of electric field) and/or the characteristics of the droplet 190 (e.g., hydrophilicity/hydrophobicity, inclusion of surfactants, solvents). By way of example, applicants have found that it can be more difficult to withdraw a droplet via the through hole 146 when the spacing between plates is relatively large (e.g., 280 μm vs. 140 μm) and/or when the sample contains methanol or one or more surfactants. For example, as the ratio of methanol to water in the droplet 190 increases, it becomes more difficult to ensure withdrawal of the droplet via the through hole 146. Likewise, the presence of a surfactant in the droplet 190 such as Pluronics, Tween 20, Brij 35, SDS, or Triton X-100, all by way of non-limiting example, can also make difficult the transfer to the electrode 115d (as shown in FIG. 2C) as the droplet is not subject to the same intermolecular repulsive forces from the hydrophobic surfaces 150, 155. Accordingly, in many instances, fluid withdrawal via a through hole 146 in the top plate could require low concentrations of organic solvents and/or surfactants and small inter-plate distances to ensure efficient transfer of the droplet 190 via the through hole 146.

With reference now to FIG. 3, however, systems and methods in accordance with the present teachings can enable the efficient transfer of fluids via a through hole formed in the top plate 340b of a digital microfluidic system 310. Though droplets 390 generally are manipulated on the exemplary microfluidic devices 110 described above within a horizontal plane between the bottom and top plates 340a,b, the sampling hole 346 (e.g., through hole or port) extending through the top plate 340b can be used to reliably extract droplets vertically by utilizing an extraction droplet 391 disposed within the sampling hole 346 to capture the sample droplet 390. By way of example, sample droplets 390 (including those containing a high concentration of organic solvents or surfactants and/or that are sandwiched between the bottom and top plates having a relatively large inter-plate distance therebetween) can be removed via the sampling hole 346 due to the intermolecular attraction between molecules in a sample droplet 390 disposed between the plates 340a,b and an extraction droplet 391 disposed within the sampling hole 346. That is, the intermolecular forces (e.g., cohesion) between the sample droplet 390 and the extraction droplet 391 can be effective to merge the fluids within the two droplets so as to form a merged droplet 392 within the sampling hole 346, as shown in FIG. 3B. With the merged droplet 392 positioned within the sampling hole 346, directly under the sampling hole 346, and/or extending above the surface of the top plate 340b (as in FIG. 3B) and despite the interruption of the actuating electric field in the vicinity of the sampling hole 346, the merged droplet 392 can then be removed (e.g., aspirated) via sampling needle 312 for transfer to a downstream analyzer. For example, the sampling needle 312 of an autosampler can be translated over and extended into the sampling hole 346 to remove the merged droplet 392. As discussed otherwise herein, the merged droplet 392 can be delivered by the autosampler to a fluid analyzer (e.g., an LC or MS).

In accordance with various aspects of the present teachings, the sample droplet 390 and extraction droplet 391 can be merged in a variety of manners. By way of example, the extraction droplet 391 can be disposed at least partially within the sampling hole 346 (e.g., with at least a portion of the volume of the extraction droplet 391 extending into the space between the bottom and top plates 340a,b), and the actuation electrodes associated with the bottom plate 340a can be actuated to bring the sample droplet 390 toward the sampling hole 346. In this manner, though it may be difficult to position the sample droplet 390 directly beneath the sampling hole 346 due to the distortions within the electric field caused by the through hole, the sample droplet can be moved into contact with the extraction droplet 391 such that the sample droplet 390 is merged therewith. Alternatively, in some aspects, the sample droplet 390 can be positioned adjacent to the sampling hole 346 prior to the extraction droplet 391 being formed therein. Thus, as the extraction droplet 391 is formed within the sampling hole 346 (e.g., dispensed into with a pre-determined volume), the extraction droplet 391 can contact a stationary sample droplet 390 such that the droplets merge and are disposed at least partially within the sampling hole 346. It will also be appreciated that the volume of the extraction droplet 391 can be increased until contact with the sample droplet 390 occurs so as to ensure capture.

The sample droplet 390 and the extraction droplet 391 can have the same or different volumes and can comprise substantially the same or different solvents. For example, the sample droplet 390 can comprise water, methanol, and/or a surfactant (as well as the sample analyte(s)), while the extraction droplet 391 can substantially comprise water.

In accordance with one aspect of the present teachings, the fluid handling system for withdrawing the merged droplet 392 as otherwise discussed herein can also be utilized to dispense the extraction droplet within the sampling hole 346. By way of example, the sample needle 312 can be fluidly coupled to a fluid reservoir and configured to inject an extraction droplet 391 within the sampling hole 346 (e.g., before or after the sample droplet 390 is translated to a specific site for extraction such as adjacent the sampling hole 346). Thus, the extraction droplet 391 could be pre-filled manually (e.g., by a user with a pipette), or deposited by the autosampler needle 312 just before the sample droplet 390 is moved toward the sampling hole 346.

Figure 4A:
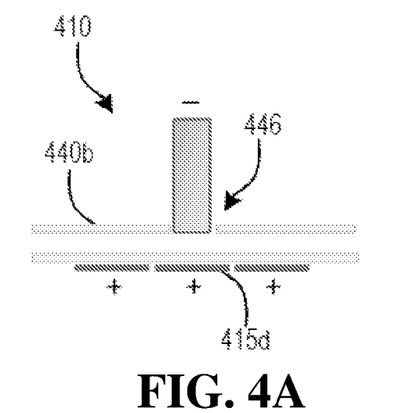
FIGS. 4A and 4B, in schematic diagram, are exemplary embodiments of a system for withdrawing a fluid droplet sandwiched between the plates of a digital microfluidic device in accordance with various aspects of the applicants' teachings.
Figure 4B:
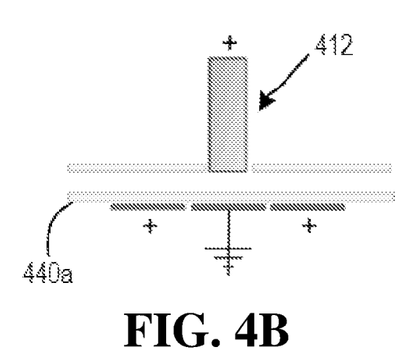

With reference now to FIG. 4, another exemplary method and system for withdrawing a fluid droplet sandwiched between the plates of a first fluid processing system is depicted. The fluid processing system 410 can be, for example, a digital microfluidic device similar to that depicted in FIG. 1, but which instead utilizes an electric potential to overcome the surface tension which prevents the withdrawal of a fluid through a sampling hole, as discussed above. For example, a metallized tip 412 of a fluid handling system to which an electric potential can be applied, can be extended into and/or through a sampling hole 446 of the top plate 440b so as to reduce distortions in the electric field in the vicinity of the sampling hole 446 caused by the lack of a reference electrode. As shown in FIG. 4A, for example, the metallized needle 412 can be extended into and/or through the sampling hole 446 and the metallized needle can have an electrical signal selectively applied thereto such that the fluid droplet can be moved to the area on the bottom plate 440a directly beneath the sampling hole 446. In some aspects, for example, an attractive electric potential relative to the bottom plate 440a (e.g., grounded or a negative potential) can be applied to the needle 412 so as to drive the sample droplet toward the needle 412. Alternatively, as shown in FIG. 4B, a positive bias can be applied to the needle 412 relative to the electrode 415d (e.g., a positive potential relative to ground). As discussed otherwise herein, the application of a control signal to the needle 412 and/or electrode 415d can thus be used to manipulate a sample fluid droplet. In various aspects, the system depicted in FIGS. 4A and 4B can eliminate the need for an extraction droplet or its merger with a sample droplet, thereby reducing sample dilution.

In accordance with various aspects of the present teachings, a sampling hole can be provided on the plate of the DMF device. In various aspects, the sampling hole can be provided through one of the top and bottom plates. A sample droplet containing an aqueous solution can be disposed between the top plate and the bottom plate of the DMF device and can be actuated to move toward the sampling hole so that the droplet can fill the sampling hole. In accordance with various aspects of the present teachings, it can be difficult for a sample droplet containing an organic solvent to enter the empty sampling hole due to its relative low surface tension. To solve this problem, the sampling hole can be first pre-filled with an aqueous solution, and then the organic sample droplet can merge with the pre-filled aqueous droplet which is an extraction droplet and remain within the sampling hole. In various aspects, the aqueous solution does not need to be limited to a pure aqueous solution, but can also be a mixture that is predominantly water but can also contain a small amount of organic solvent or any suitable mixture can be used. In various aspects, the sample droplet can comprise a mixture of water and an organic solvent. In various aspects, the organic solvent can be, but is not limited to, methanol, acetonitrile, ethanol, and propanol. In various aspects, the sample droplet can comprise a mixture of about 70% water and about 30% organic solvent. In various aspects, the sample droplet can comprise a mixture of about 70% water and about 30% methanol. In various aspects, the sample droplet comprises a surfactant.

In accordance with various aspects of the applicant's teachings, a method of processing a sample is provided comprising disposing a sample droplet between a top plate and a bottom plate of a digital microfluidic device, and removing at least a portion of the droplet from the digital microfluidic device via a sampling hole extending through the plate.

In accordance with various aspects, the method further can comprise pre-filling the sampling hole with an aqueous solution to form an extraction droplet in the sampling hole, contacting the sample droplet and the extraction droplet with one another so as to form a merged droplet at least partially disposed in the sampling hole, wherein at least a portion of the merged droplet is removed from the digital microfluidic device via the sampling hole. In accordance with various aspects, the aqueous solution does not need to be limited to a pure aqueous solution, but can also be a mixture that is predominantly water but can also contain a small amount of organic solvent or any suitable mixture can be used.

In accordance with various aspects, the method further can comprise transferring the merged droplet to an analysis device.

In some aspects, the method further can comprise moving the sample droplet toward the sampling hole by actuating one or more actuation electrodes associated with the bottom plate. In some aspects, moving the sample droplet toward the sampling hole can comprise manipulating the sample droplet to be disposed adjacent the sampling hole.

In some aspects, a plurality of actuation electrodes can be disposed within the bottom plate, and actuating the plurality of actuation electrodes can comprise controlling the voltages applied to the different actuation electrodes so as to move the sample droplet. In some aspects, at least one of the top and bottom plates can comprise an electrode array configured to manipulate movement of the sample droplet.

In various aspects, the method further can comprise increasing a volume of the extraction droplet until the extraction droplet contacts the sample droplet.

In some aspects, removing the merged droplet from the digital microfluidic device can comprise aspirating the merged droplet via the sampling hole by extending a sampling needle into the merged droplet through the sampling hole.

In some aspects, an autosampler can be utilized to form the extraction droplet in the sampling hole.

In some aspects, the sample droplet can comprise a mixture of water and an organic solvent. In some aspects, the sample droplet can comprise a mixture of about 70% water and about 30% methanol. In some aspects, the sample droplet can comprise a surfactant.

In accordance with various aspects, a system for processing a sample is provided that includes a digital microfluidic device, comprising opposed top and bottom plates defining a space therebetween for containing a sample droplet, the plate having a sampling hole, and a fluid handling system can be configured to extract at least a portion of the droplet from the digital microfluidic device via the sampling hole.

In accordance with various aspects, the system further can comprise the sampling hole extending therethrough in fluid communication with the space, the sampling hole can be configured to receive an extraction droplet comprising an aqueous solution, a plurality of actuation electrodes can be associated with at least one of the top and bottom plates, wherein the plurality of actuation electrodes can be configured to manipulate the sample droplet such that the sample droplet and the extraction droplet contact one another so as to form a merged droplet at least partially disposed in the sampling hole, wherein at least a portion of the merged droplet can be extracted from the digital microfluidic device via the sampling hole. In accordance with various aspects, the aqueous solution does not need to be limited to a pure aqueous solution, but can also be a mixture that is predominantly water but can also contain a small amount of organic solvent or any suitable mixture can be used.

In accordance with various aspects, the system further can comprise an analysis device configured to receive the extracted merged droplet from the fluid handling system. In various aspects, the fluid handling system can comprise an autosampler. In various aspects, the fluid handling system further can be configured to form the extraction droplet within the sampling hole, the plurality of actuation electrodes can be configured to move the sample droplet adjacent to the sampling hole, and the fluid handling system can be configured to form the extraction droplet in said sampling hole with a sufficient volume such that said extraction droplet contacts said sample droplet, and the fluid handling system can be configured to increase a volume of the extraction droplet until the extraction droplet contacts the sample droplet.

In accordance with various aspects, the system further can comprise at least one memory operatively coupled to the controller, the at least one memory can be configured to store at least one sample processing protocol for execution by the controller.

In accordance with various aspects, a method of processing a fluid can be provided comprising disposing a sample droplet between a top plate and a bottom plate, extending a sampling needle into a sampling hole extending through one of the top and bottom plate in a position opposed to an electrode associated to the other of the top and bottom plate, applying an electric potential to at least one of the sampling needle and the electrode so as to generate an electric field in the space between the top and bottom plates in the position, removing at least a portion of the merged droplet from the sampling hole, aspirating the sample droplet while applying the electric potential, and biasing the sampling needle relative to the electrode so as to attract the sample droplet.

EXAMPLES

Figure 5:
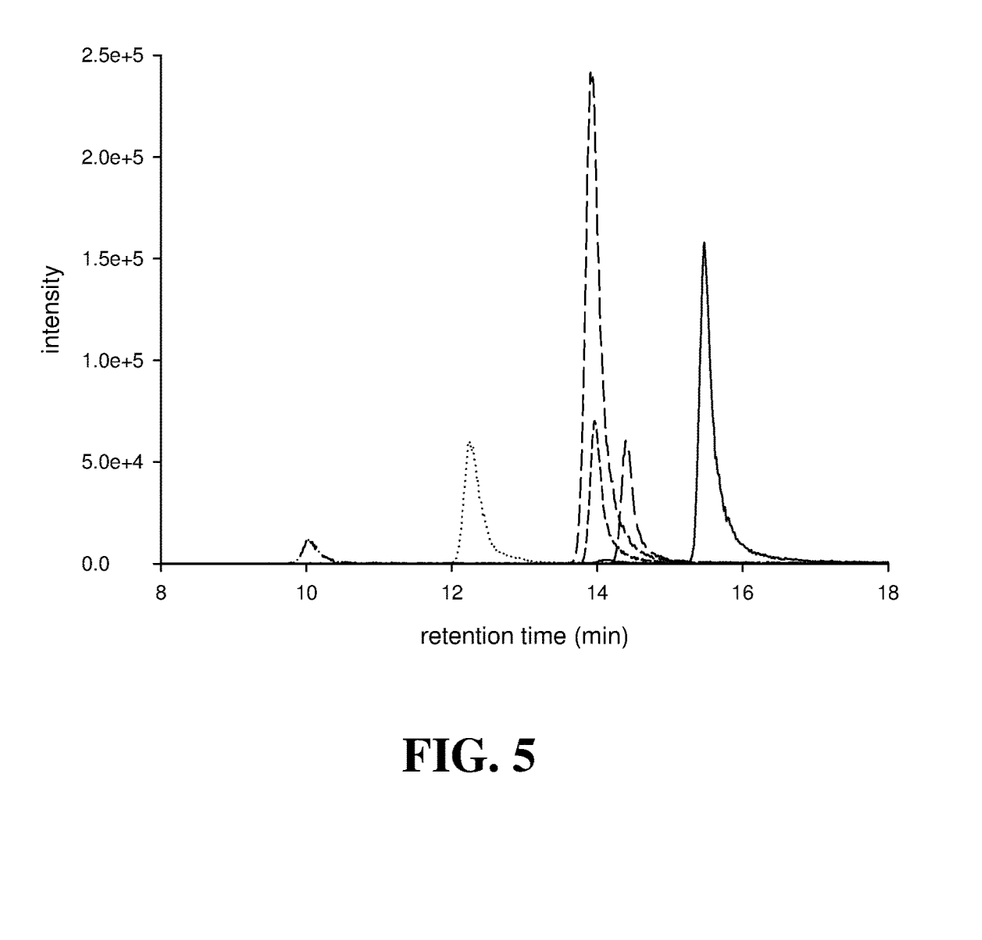
FIG. 5 depicts an exemplary mass chromatogram utilizing a system in accordance with various aspects of the applicants' teachings.

The above teachings will now be demonstrated using the following example, provided to demonstrate but not limit the present teachings. With reference now to FIG. 5, an exemplary mass chromatogram is depicted in which a sample is subjected to an in-line beta-galactosidase digest within a digital microfluidic device (as depicted schematically in FIG. 3), transferred from the digital microfluidic device, injected into an LC-MS/MS system, and subjected to analysis by LC-MS/MS to detect MRM transitions.

The volume of the extraction droplet within the sampling hole was 5 μL, which contained 12.5 fmol/μL beta-galactosidase digest (in $H_2O$/ACN/formic acid 98:2:0.1). The Eksigent NanoLC-AS1 Autosampler was used to withdraw the extraction droplet and deliver 1 μL of the sample from a prototype DMF device to a nano-LC-MS/MS system (Eksigent nanoLC 1D plus—AB SCIEX QTRAP 5500) for analysis.

The results disclosed herein demonstrate the utility of the present teachings for multiplexed, high throughput, and/or automated sample processing/preparation with digital microfluidic devices, and without user intervention (e.g., off-line manual fluid transfer steps to a downstream analyzer) that could lead to adsorption, contamination, and/or sample loss.

Figure 6:
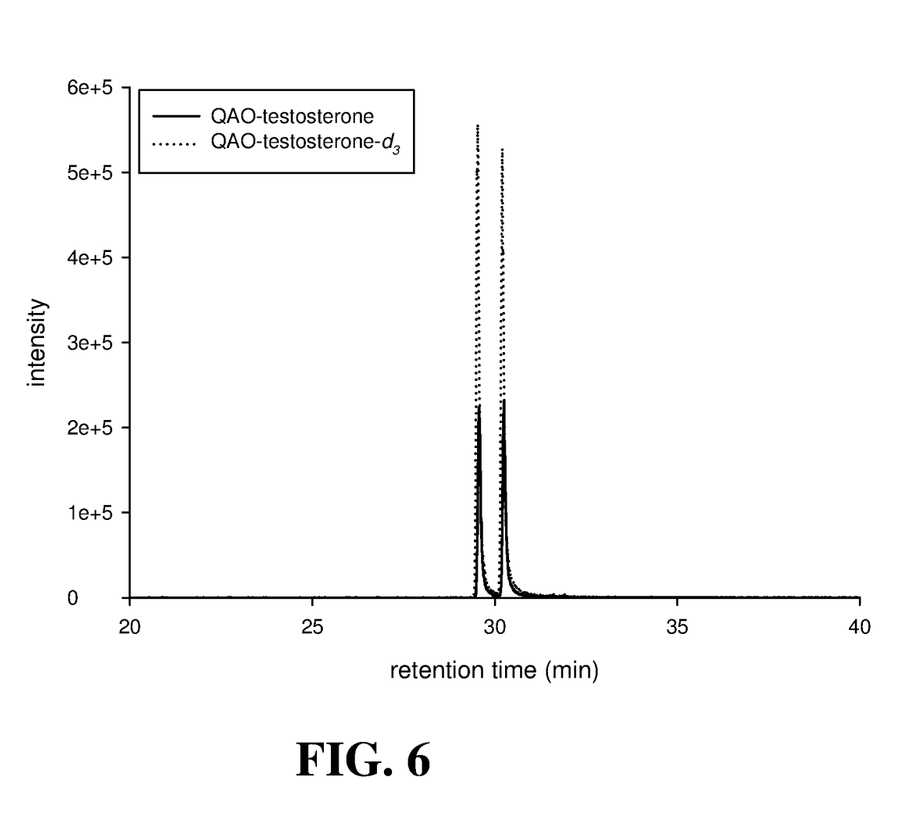
FIG. 6 depicts an exemplary mass chromatogram utilizing a system in accordance with various aspects of the applicants' teachings.

With reference now to FIG. 6, an exemplary mass chromatogram is depicted showing the analysis of a merged droplet from a methanol droplet containing QAO-testosterone and an aqueous droplet containing QAO-testosterone-$d_3$ by a DMF-LC-MS/MS system. The sampling hole was pre-filled with a 5-μL aqueous droplet containing 10 ng/mL QAO-testosterone-$d_3$ to merge with a 2-μL methanol droplet containing 10 ng/mL QAO-testosterone on a DMF device. The merged droplet was analyzed with the DMF-LC-MS/MS system. As shown in FIG. 6, the intensity ratio of QAO-testosterone-$d_3$ versus QAO-testosterone was approximately 5:2, indicating the uniform distribution of both components in the merged droplet. Derivatization of testosterone can lead to structural isomers that are separable via LC-MS/MS, which were observed as two separable chromatographic peaks.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The section headings used herein are for organizational purposes only and are not to be construed as limiting. While the applicants' teachings are described in conjunction with various embodiments, it is not intended that the applicants' teachings be limited to such embodiments. On the contrary, the applicants' teachings encompass various alternatives, modifications, and equivalents, as will be appreciated by those of skill in the art.

The invention claimed is:

1. A method of processing a sample comprising:
   disposing a sample droplet between a top plate and a bottom plate of a digital microfluidic device, one of the top plate and bottom plate having a sampling hole, and
   pre-filling the sampling hole with an aqueous solution from a needle or pipette to form an extraction droplet in the sampling hole,
   contacting the sample droplet and the extraction droplet with one another so as to form a merged droplet at least partially disposed in the sampling hole, wherein the needle or pipette removes at least a portion of the merged droplet by aspiration from the digital microfluidic device via the sampling hole.

2. The method of claim 1, further comprising transferring the merged droplet to an analysis device.

3. The method of claim 1, further comprising moving the sample droplet toward the sampling hole by actuating one or more actuation electrodes associated with the bottom plate.

4. The method of claim 3, wherein moving the sample droplet toward the sampling hole comprises manipulating the sample droplet to be disposed adjacent the sampling hole.

5. The method of claim 3, wherein a plurality of actuation electrodes are disposed within the bottom plate, and wherein actuating the plurality of actuation electrodes comprises controlling the voltages applied to the different actuation electrodes so as to move the sample droplet.

6. The method of claim 1, wherein at least one of the top and bottom plates comprises an electrode array configured to manipulate movement of the sample droplet.

7. The method of claim 1, further comprising increasing a volume of the extraction droplet until the extraction droplet contacts the sample droplet.

8. The method of claim 1, wherein the needle or pipette is part of an autosampler.

9. The method of claim 1, wherein the sample droplet comprises a mixture of water and an organic solvent.

10. The method of claim 9, wherein the sample droplet comprises a mixture of about 70% water and about 30% methanol.

11. The method of claim 1, wherein the sample droplet comprises a surfactant.

* * * * *